United States Patent [19]

Billard

[11] Patent Number: 4,754,151

[45] Date of Patent: Jun. 28, 1988

[54] METHOD AND APPARATUS FOR MEASURING THE OPTICAL SCATTERING CO-EFFICIENT OF THE OCEAN USING LARGE AND SMALL FIELDS OF VIEW

[75] Inventor: Brian Billard, Redwood Park, Australia

[73] Assignee: The Commonwealth of Australia, Canberra, Australia

[21] Appl. No.: 887,804

[22] PCT Filed: Nov. 8, 1985

[86] PCT No.: PCT/AU85/00272

§ 371 Date: Jul. 8, 1986

§ 102(e) Date: Jul. 8, 1986

[87] PCT Pub. No.: WO86/03003

PCT Pub. Date: May 22, 1986

[30] Foreign Application Priority Data

Nov. 9, 1984 [AU] Australia .............................. PG8062

[51] Int. Cl.$^4$ .............................................. G01N 15/07
[52] U.S. Cl. ....................................... 250/574; 356/342
[58] Field of Search .................... 250/560, 574; 356/1, 356/4, 342, 343

[56] References Cited

U.S. PATENT DOCUMENTS

| | | | |
|---|---|---|---|
| 3,669,540 | 6/1972 | Rattman et al. | 356/4 |
| 3,777,167 | 12/1973 | Shepherd | 250/560 |
| 3,781,552 | 12/1973 | Kadrmas | 356/4 |
| 4,257,705 | 3/1981 | Hosoe et al. | 356/1 |
| 4,518,254 | 5/1985 | Penny et al. | 356/4 |
| 4,647,193 | 3/1987 | Rosenfeld | 356/4 |

FOREIGN PATENT DOCUMENTS

WO82/01075 4/1982 PCT Int'l Appl. .

OTHER PUBLICATIONS

Naval Engineers Journal, Apr. 1980—Hydrographic Airborne Laser Sounder—pp. 54–60.
Applied Topics, vol. 19, No. 6, Mar. 15, 1980—Water Depth Measurement Using an Airborne Pulsed Neon Laser System, by F. E. Hoge, et al—pp. 871–883.
Marine Environmental Research 4 (1980-1981), 65-7-9—Simultaneous Measurements of Transparency and Irradiance in the Coastal Waters of North Wales—B. J. Topliss, et al.
Translation from Zhurnal Prikladnoi Spektroskopii, vol. 29, No. 4, pp. 710–716, Sep. 16, 1977—Features of the Measurement of the Extinction and Absorption Coefficients of Water by Pulsed Probing, A. P. Ivanov et al.
SPIE, vol. 208, Ocean Optics VI (1979), pp. 64–72—Spreading of Light Beams in Ocean Water—W. H. Wilson.
Aust. J. Phys. 1984, 37, 75–90—pp. 75–90—A Theoretical Study of an Airborne Laser Technique for Determining Sea Water Trubidity—D. M. Phillips, et al.

Primary Examiner—David C. Nelms
Assistant Examiner—William L. Oen
Attorney, Agent, or Firm—Cushman, Darby & Cushman

[57] ABSTRACT

The method of measuring the optical scattering co-efficient of the ocean by means of a laser beam (15) from a platform (16) above the ocean surface (3) in which an ocean penetrating beam (15) is swept across the direct path of travel to the surface of the ocean (3) and through it to the ocean bottom (4) to be back-reflected to the ocean surface (3) and to a receiver on the platform (16) characterized by changing the field of view to alternately use a small and a large field of view and calculating from the larger field of view an estimate of the absorption co-efficient and from the smaller field of view an estimate of beam attenuation co-efficient.

9 Claims, 3 Drawing Sheets

METHOD AND APPARATUS FOR MEASURING THE OPTICAL SCATTERING CO-EFFICIENT OF THE OCEAN USING LARGE AND SMALL FIELDS OF VIEW

FIELD OF THE INVENTION

This invention relates to a method and apparatus means for measuring the optical scattering coefficient of the ocean by means of a laser beam used from a platform for measuring ocean depth.

BACKGROUND OF THE INVENTION

The development of a system for laser hydrography that has sufficient accuracy to meet the standard requirements of the international hydrographic community must incorporate an allowance for the variation (mostly elongation) of the effective path length of the laser beam as it passes through the sea. The variation arises as light photons interact with particles and other scattering centers within the body of the ocean, and are either absorbed or scattered in a possibly different direction to the direction of incidence.

The effective net path variation, as viewed by an airborne receiver, will depend on sea depth, the scan angle at which the laser pulse is fired relative to the local vertical, the concentration and nature of hydrosols within the ocean causing scattering of the laser beam, as well as a number of other factors.

This general field was described in the specification of a Patent Application field under the Patent Cooperation Treaty, International Publication Number WO 82/01075 which related to Ocean Depth sounding from the air by laser beam which used a red and green laser beam and received reflected signals back by means of a pair of telescopes, one receiving the infrared signal and the other the green signal. The work which resulted in the Application was undertaken by what is known as the WRELADS group of the Defense Department of the Commonwealth of Australia.

Analysis of the large bank of data collected by the WRELADS laser hydrographic system shows that consideration of sea depth and scan angle are not sufficient to meet accuracy requirements, and that account must be taken of temporal as well as geographic variations in sea turbidity.

Sea turbidity can be chracterized by what is commonly referred to as the inherent optical properties. These are the absorption coefficient "a", the scattering coefficient "b", and the volume scattering function ($\beta(\theta)$, where $\theta$ is the angle of scattered photon to its direction of incidence on a scattering center). The volume scattering function is on many occasions approximated by the two components $$b_f = 2\pi \int_0^{\frac{\pi}{2}} \beta(\theta)\sin\theta d\theta, \text{ and}$$

$$b_b = 2\pi \int_{\frac{\pi}{2}}^{\pi} \beta(\theta)\sin\theta d\theta,$$

$b_f$ and $b_b$ are referred to as the forward scattering and the backscatter coefficients respectively, and the forward scatter is generally very much greater than the backscatter.

This invention describes a method for the real time estimation of the scatter "b" by airborne laser hydrographic systems to an accuracy sufficient for incorporation within a predictive model of the process of photon path variation by scattering.

It is noted that the process of backscatter within the sea bulk will lead to the detection by an airborne system of what is commonly referred to as a backscatter envelope. Studies from both a theoretical basis and an experimental basis as carried out by WRELADS show that the shape of this envelope under normal conditions of a uniform mixture of hydrosols within the vertical column of seawater traversed by the laser beam is of an initial high point followed by an exponential decay. Under conditions of constant system gain and laser power, the peak height of the envelope will be proportional to the backscatter coefficient. The exponential decay is characterized by the decay constant 2k, which is referred to as the attenuation coefficient.

Theoretical studies, using Monte Carlo techniques and assumed volume scattering functions, have shown that "k" is a function of both "a" and "b", but under normal conditions in hydrographic laser systems such as WRELADS, the field of view of the receiver is sufficiently large for k=a to be a good approximation. These theoretical studies also show, however, that in the limit of a very small field of view, then "k" approaches c=a+b. "c" is sometimes referred to as the total (or beam) attenuation coefficient, since it represents the decay constant for energy in the laser beam associated with photons that have been neither scattered nor absorbed as they pass downwards through the sea.

Studies to date using WRELADS data have concentrated on using measurements of "k", and hence "a", together with a parameter proportional to the backscatter envelope amplitude, and hence $b_b$ to make inferences about changes in "b", and hence in the light path variation. However, while these studies have shown that these inherent optical properties may be functionally linked within a limited time and space, the link is insufficient to make the general inferences that would be required in an operational system of air borne laser hydrography.

SUMMARY OF THE INVENTION

In the invention described herein, changes in "b" will be monitored more directly by analysis of the decay constants of the back scatter envelopes resulting from the use of the two different receiver fields of view. The large field of view will give a estimate of the absorption coefficient "a", while a small field of view will give a decay constant "k" from which may be deduced a value of "b".

The advantages of this method are that it more directly measures "b", the optical property most closely associated with the process of path variation by scattering, without having to rely on inferences of proportionality to $b_b$, the backscatter coefficient—which inferences have now been demonstrated to be valid only within limited regimes. Secondly, the measurement of the decay constant for a backscatter envelope is independent of the effective system gain, which has proved very difficult to calibrate in WRELADS studies of $b_b$.

Tests done with various fields of view using the WRELADS system have shown that fields of view can be selected that are sufficiently large to receive a measurable backscatter envelope while being sufficiently small to observe the effect described above.

Thus it will be seen that this invention is novel in its use of two receiver fields of view to measure forward scatter from an airborne platform for use in laser hydrography and other scientific oceanographic applications.

BRIEF DESCRIPTION OF THE DRAWINGS

In order however that the nature of the invention will be fully appreciated an embodiment thereof will now be described with reference to the accompanying drawings to details of which the invention need however not necessarily be limited.

In the drawings.

DETAILED DESCRIPTION OF THE INVENTION

Figure 1:
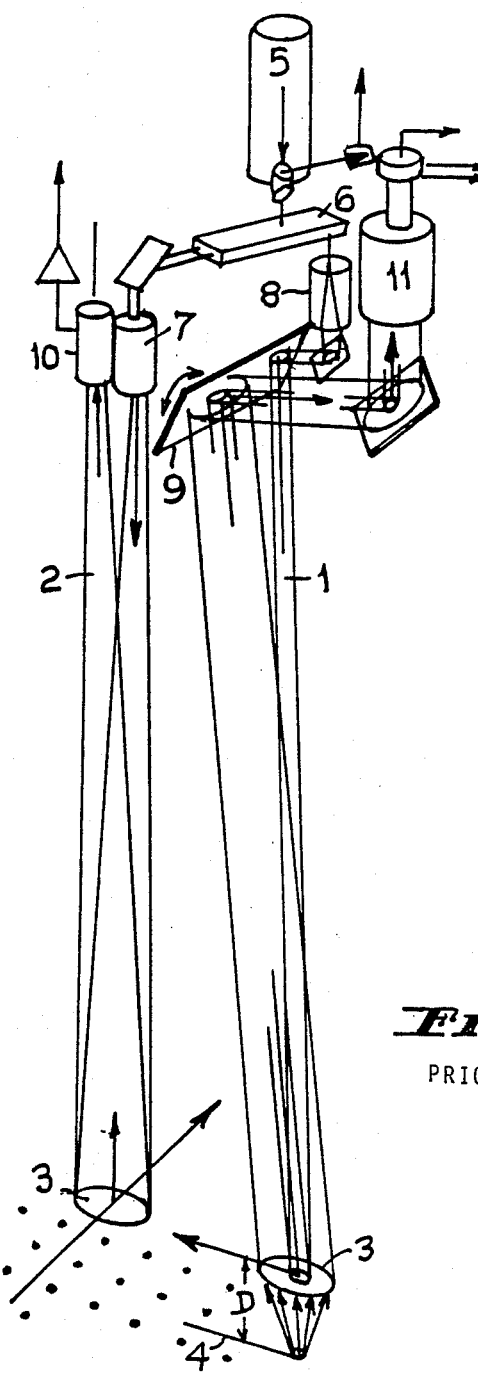
FIG. 1 is a schematic view of an ocean depth sounding device which uses laser beams from a platform positioned above the surface of the ocean, the depth of which is to be measured, this view depicting the general prior art as disclosed in International Publication No. WO82/01075 by the same applicants.

It will be realized from FIG. 1 that the green pulse scans the ocean floor over a substantial area transversely to the direction of travel so that an average reading of ocean depth results by the depth scanned whereas the infrared pulse which measures the surface distance is steady as the surface position varies only by tidal and wave motion whereas the ocean bottom may vary substantially in its depth over the traverse of the lateral scan.

It will be seen from the prior art document that the green beam 1 and the infrared beam 2 are both measured at the surface 3 but the green beam is also measured at the bottom 4 to give a depth of water differential. The beams are produced by a laser 5 acting through a coupling 6 to direct the steady infrared pulse through the telescope 7 to the ocean surface and the green pulse through the telescope 8 to the scanning mirror 9. The red pulse is detected by the telescope 10 and the green pulse is detected by the telescope 11 through the scanning mirror and these pulses are then processed to give the ocean depth.

Figure 2:
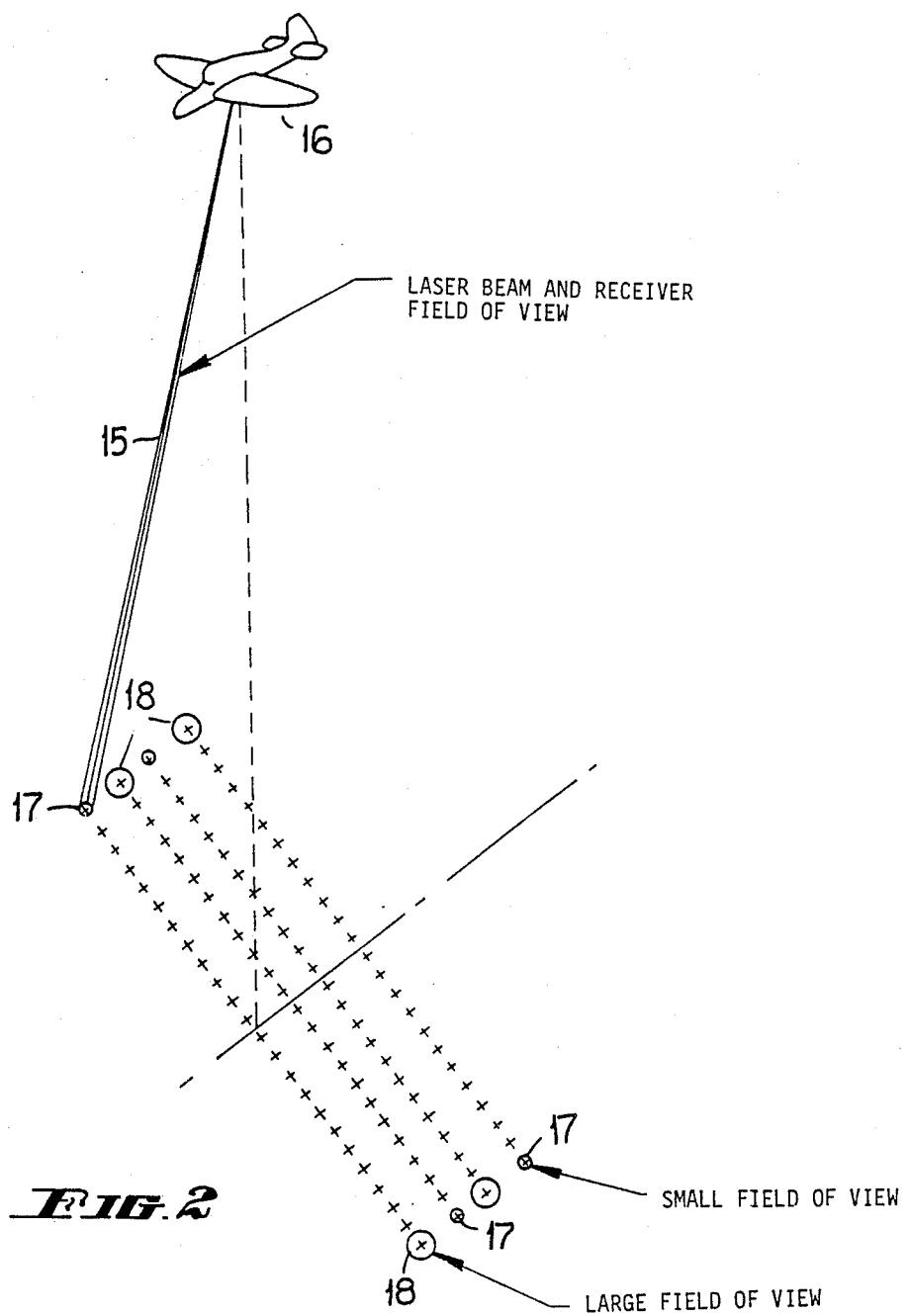
FIG. 2 is a schematic view showing how the ocean depth measuring beam scans the ocean bottom generally normally to the direction of travel of the platform and at the end of each traverse alternately reads a large field of view and a small field of view.

In the present invention, as shown in FIG. 2, the green beam 15 is directed from the platform 16 to the ocean bottom but at the commencement of one traverse a reading is taken on a small field of view as indicated at 17 and at the other end of the traverse a large field of view reading is taken as indicated at 18.

The same method of reading the return pulses can be used as indicated in FIG. 1 and from that view it will be seen that the green beam which penetrates the ocean surface spreads on the return deflection to be readable over a relatively large area at the ocean surface 3. According to the present invention, whereas in the prior art case a uniform dimension surface scan is being read, at the end of each traverse either a large field of view is scanned or a small field of view and this then allows the calculation of the present invention to be effected to very materially increase the accuracy of the reading of depth of the ocean.

Figure 3:
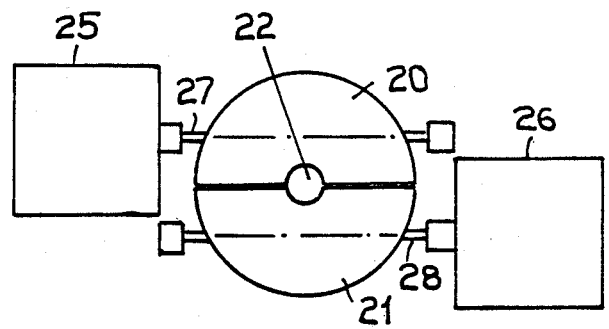
FIG. 3 is a schematic drawing showing in front elevation how the field of view may be changed by a pair of shutters.
Figure 4:
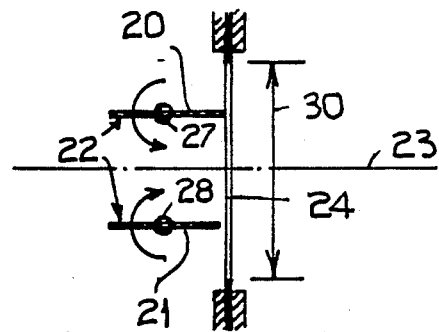
FIG. 4 is a sectional view at right angles to FIG. 3 showing the shutters in the open position where the large field of view is effective.

The device of this invention comprises a pair of shutters 20 and 21 which in FIG. 3 are shown in the closed position so that the shutters 20 and 21 reduce the field of view to the small field of view given by the circular aperture 22. In the position shown in FIG. 4, the shutters 20 and 21 are in parallel alignment with the axis 23 of the beam and the aperture 30 is now defined by the iris 24 which may if required be selectable to define the maximum aperture required at the particular time.

The shutters 20 and 21 are driven respectively by stepper motors 25 and 26 which have shafts 27 and 28 which carry the shutters. The stepper motors 25 and 26 can readily be actuated by any known type of signal to alternately position the shutters as the beam reaches the end of a traverse.

The shutters 20 and 21 are located in an aperture 30 in the return green beam and are preferably positioned adjacent to the telescope which receives the green return beam.

The claims defining the invention are as follows:

I claim:

1. A method of measuring the optical scattering co-efficient of the ocean by using a laser disposed on a platform above the ocean surface, the method comprising the steps of:
    directing an ocean penetrating beam, emanating from the laser, to the surface of the ocean and through to the ocean bottom, said beam being reflected back from the ocean bottom to a receiver on the platform;
    sweeping said beam transversely across the direction of movement of the platform, by changing the field of view at first and second selected positions of the sweep to alternately use a first field of view of one dimension and then use a second field of view of a substantially different dimension;
    calculating from the larger field of view an estimate of the absorption co-efficient; and
    calculating from the smaller field of view an estimate of beam attenuation co-efficient.

2. The method of claim 1 in which the said first position is at one end of a sweep and the said second position is at the other end of the sweep.

3. Apparatus for measuring the optical scattering co-efficient of the ocean including a laser disposed on a platform above the ocean surface, said apparatus comprising:
    means for directing the laser to generate an ocean penetrating beam to the surface of the ocean and through to the ocean bottom, the ocean penetrating beam being back-reflected from the ocean bottom to the ocean surface;
    a receiver disposed on the platform for receiving the back-reflected ocean penetrating beam as a reflected beam;
    sweeping means disposed on the platform for sweeping the ocean penetrating beam transversely across the direction of movement of the platform;
    view changing means for periodically and alternately changing the field of view to receive a first field of view of one dimension and then a second field of view of a second dimension larger than said one dimension, the larger field of view being used to calculate an estimate of the absorption and the smaller field of view being used to calculate an estimate of beam attenuation.

4. Apparatus for measuring the optical scattering co-efficient of the ocean according to claim 3 wherein the view changing means comprises shutter means disposed in the path of the reflected beam and driven to define a small field of view in one position and a large field of view in another position.

5. Apparatus for measuring the optical scattering co-efficient according to claim 4 wherein said shutter means comprises a pair of shutters, mounted on shafts, said shutters dimensioned to extend across a larger aperture through which said reflected beam is arranged to pass, said shutters having a smaller aperture defined by said shutters when said shutters are positioned to extend across said larger aperture normal to the axis of the reflected beam and to be movable to be parallel to said axis when the larger field of view is required.

6. Apparatus for measuring the optical scattering co-efficient according to claim 4 in which said shutters are driven by a pair of stepper motors on said shafts on which said shutters are mounted.

7. Apparatus for measuring the optical scattering co-efficient according to claim 5 wherein the said aperture has an iris diaphragm to allow selection of the dimension of the larger field of view.

8. Apparatus for measuring the optical scattering co-efficient according to claim 5 in which said shutters are driven by a pair of stepper motors on said shafts on which said shutters are mounted.

9. Apparatus for measuring the optical scattering co-efficient according to claim 6 wherein said aperture has an iris diaphragm to allow selection.

* * * * *